United States Patent [19]

Hillebrecht et al.

[11] 4,319,912

[45] Mar. 16, 1982

[54] PHOSPHONATE HERBICIDAL ANTIDOTES

[75] Inventors: Wayne R. Hillebrecht, Pleasanton, Calif.; Felice J. Calderoni, Monroe, Conn.

[73] Assignee: Stauffer Chemical Company, Westport, Conn.

[21] Appl. No.: 141,868

[22] Filed: Apr. 21, 1980

[51] Int. Cl.$^3$ .................. A01N 57/02; A01N 57/20
[52] U.S. Cl. .............................. 71/86; 260/953; 260/967
[58] Field of Search .................................. 71/86

[56] References Cited

U.S. PATENT DOCUMENTS 4,021,224  5/1977  Pallos et al. .................. 71/88

Primary Examiner—Anton H. Sutto
Attorney, Agent, or Firm—Harry A. Pacini

[57] ABSTRACT

Compositions comprising compounds of the formula

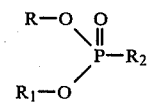

in which
R and $R_1$ are independently selected from the group consisting of alkyl having 1–4 carbon atoms and haloalkyl having 1–4 carbon atoms; and
$R_2$ is selected from the group consisting of hydrogen and halohydroxyalkyl having 1–4 carbon atoms; and

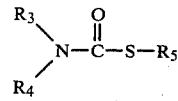

in which
$R_3$ is selected from the group consisting of alkyl having 1–6 carbon atoms and alkenyl having 2–6 carbon atoms;
$R_6$ is selected from the group consisting of alkyl having 1–6 carbon atoms, alkenyl having 2–6 carbon atoms, cyclohexyl and phenyl; or
$R_3$ and $R_4$ together form an alkylene group having 5–10 carbon atoms; and
$R_5$ is selected from the group consisting of alkyl having 1–6 carbon atoms, haloalkyl having 1–6 carbon atoms, cycloalkyl having 5–10 carbon atoms, phenyl, substituted phenyl, wherein the substituents are alkyl having 1–4 carbon atoms, haloalkyl having 1–4 carbon atoms, and halo, benzyl and substituted benzyl, wherein the substituents are alkyl having 1–4 carbon atoms, haloalkyl having 1–4 carbon atoms, and halo are useful for the protection of crops from thiocarbamate herbicidal injury.

12 Claims, No Drawings

PHOSPHONATE HERBICIDAL ANTIDOTES

BACKGROUND OF THE INVENTION

Uses of Herbicides

A herbicide is a compound which controls or modifies plant growth, e.g., killing, retarding, defoliating, desiccating, regulating, stunting, tillering, stimulating, and dwarfing, and the like. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the beneficial crop and selectivity toward weeds. Certain herbicidal compounds are phytotoxic to some weed species but not to others.

A manufacturer of a herbicide generally recommends range of rates and concentrations calculated to maximize weed control. The range of rates usually varies from approximately 0.01 to approximately 50 pounds per acre (lb/A) (0.0112 to 56 kilograms per hectare (k/ha)), usually from 0.1 to 25 lb/A (0.0112 to 28 k/ha). The actual amount used depends upon several considerations, including, crop tolerance, particular weed susceptibility and overall cost limitations.

Some herbicides display-exclusive selectivity toward weed species. Many are toxic to both weeds and the intended crop beneficiary. Therefore, a particular herbicide may proscribe its injurious effect on the cultivated crop even though it may otherwise provide excellent control of weeds found in the crop field.

To preserve the beneficial aspects of herbicide use and to mitigate crop damage, many herbicidal antidotes have been prepared. These antidotes reduce or eliminate damage to the crop without substantially impairing the beneficial effect of the herbicide. For example, see U.S. Pat. Nos. 4,021,224 and 4,021,229 and Belgian Pat. No. 846,894.

Although several explanatory theories have been advanced, the precise mechanism by which an antidote reduces herbicidal injury has not been clearly established. An antidote compound may in fact be a remedy, interferent, protectant, or antagonist. As used herein, "antidote" describes, i.e., the continued effect of establishing herbicidal selectivity of herbicidal phytotoxicity to weed species and reduced or non-phytotoxicity to cultivated crop species.

As an alternative mode of action, the compounds of this invention may interfere with the normal herbicidal action of the thiocarbamate-type herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide antidotes or antidotal amount is meant to describe that effect or the amount which produces the effect which tends to counteract the normal injurious herbicidal response that the herbicide might otherwise produce. Whether it is to be termed a remedy, interferent, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

Thiocarbamate, herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, their beneficial use can be enhanced by the addition of an antidotal compound.

DESCRIPTION OF THE INVENTION

It has been discovered that certain phosphonate compounds are effective antidotes for the protection of crops from thiocarbamate herbicidal injury. These compounds have the formula:

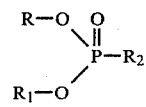

in which
R and $R_1$ are independently selected from the group consisting of alkyl having 1–4 carbon atoms, preferably methyl, and haloalkyl having 1–4 carbon atoms, preferably dibromopropyl; and
$R_2$ is selected from the group consisting of hydrogen and halohydroxyalkyl having 1–4 carbon atoms, preferably 2,2,2-trichloro-1-hydroxyethyl.

This invention embodies a herbicidal composition comprising:

(a) an antidotally effective amount of a compound of the formula:

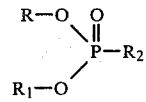

in which
R and $R_1$ are independently selected from the group consisting of alkyl having 1–4 carbon atoms, preferably methyl, and haloalkyl having 1–4 carbon atoms, preferably dibromopropyl; and
$R_2$ is selected from the group consisting of hydrogen and halohydroxyalkyl having 1–4 carbon atoms, preferably 2,2,2-trichloro-1-hydroxyethyl; and (b) a herbicidally effective amount of a thiocarbamate of the formula:

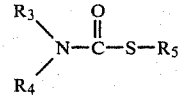

in which $R_3$ is selected from the group consisting of alkyl having 1-6 carbon atoms and alkenyl having 2-6 carbon atoms;

$R_4$ is selected from the group consisting of alkyl having 1-6 carbon atoms, alkenyl having 2-6 carbon atoms, cyclohexyl and phenyl; or $R_3$ and $R_4$ taken together form an alkylene group having 5-10 carbon atoms; and $R_5$ is selected from the group consisting of alkyl having 1-6 carbon atoms, haloalkyl having 1-6 carbon atoms, cycloalkyl having 5-10 carbon atoms, phenyl, substituted phenyl, wherein the substituents are alkyl having 1-4 carbon atoms, haloalkyl having 1-4 carbon atoms and halo, benzyl, and substituted benzyl, wherein the substituents are alkyl having 1-4 carbon atoms, haloalkyl having 1-4 carbon atoms and halo.

The terms "alkyl" and "alkenyl" as used herein are intended to include both straight- and branched-chain groups. The term "halo" is intended to include mono- and polyhalo groups and includes, chloro, bromo, iodo, fluoro and mixtures thereof. All carbon atom ranges are intended to be inclusive of both upper and lower limits. Exemplary of "alkyl" are methyl, ethyl, n-propyl, isopropyl, n-butyl, isobutyl, tertiarybutyl, pentyl, hexyl, and the like. Exemplary of "alkenyl" are such groups as vinyl, proenyl, butenyl, pentyl, hexenyl and the like. Exemplary of cycloalkyl are cyclopentyl, cyclohexyl, 2,2-dimethyl cyclohexyl, cycloheptyl and the like.

By way of exemplification, the active thiolcarbamate herbicides employed in the invention may include the following: EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, S-ethyl hexahydro-1H-azepine-1-carbothioate, S-4-chlorobenzyl diethyl thiocarbamate, and combinations thereof.

This invention also includes the method of protecting crops from herbicidal injury which comprises applying to the locus where protection is desired a nonphytotoxic antidotally effective amount of a compound of the formula:

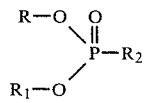

in which

R and $R_1$ are independently selected from the group consisting of alkyl having 1-4 carbon atoms, preferably methyl, and haloalkyl having 1-4 carbon atoms, preferably dibromopropyl; and $R_2$ is selected from the group consisting of hydrogen and halohydroxyalkyl having 1-4 carbon atoms, preferably 2,2,2-trichloro-1-hydroxyethyl.

Preparation

The thiocarbamates of the present compositions can be prepared by the procedures described in U.S. Pat. Nos. 2,913,327, 3,185,720, 2,983,747, 3,133,947 and 3,198,786.

O,O-dimethyl(2,2,2-trichloro-1-hydroxyethyl)phosphonate can be prepared by the procedures described in expired U.S. Pat. No. 2,701,225. It is also commercially available as an insecticide under a variety of brand names, such as Dylox®, Dipterex®, Anthon®, Neuvgon®, Tugon®, and Trichlorfon.

The dibromopropyl phosphonates may be prepared by the procedures described by Abramov, V. S. and A. L. Shalman, Khim. Org. Soedin Fosfora, Akad. Nauk. SSSR, Otd. Obshch. Tekh. Khim. 1967, 115-19, cited at 69 *Chemical Abstracts* 67486b (1968).

Bis-(1,3-dibromoisopropyl) phosphonate may also be prepared in the following manner.

To 81.2 grams (g.) or 0.3 mole (m.) of phosphorus tribromide, cooled in an ice bath, 82.2 g. (0.6 m.) epibromohydrin was added dropwise. Then 5.4 g. of water was added to produce hydrogen phosphonate. The mixture was stirred for three hours. Vacuum aspiration yielded 162 g. of a clear, colorless semi-viscous liquid.

Methylene chloride (150 milliliters (ml.)) was added to the product which was then washed twice with 100 ml. of saline solution, once with sodium bicarbonate solution, and once again with saline solution. The organic layer was separated and dried over anhydrous magnesium sulfate. Filtering and stripping yielded 139 g. (96% of theoretical yield) of bis-(1,3-dibromoisopropyl) phosphonate ($n_D^{30}$ 1.5630. Structure was confirmed by infrared analysis.

Testing

Stock solutions of the herbicides were prepared by diluting the requisite amount of each formulated herbicide in water. The solution compositions and application rates and methods are summarized in Table I.

TABLE I

| | Herbicide Stock Solutions | | | |
|---|---|---|---|---|
| | Composition | | Application | |
| | Herbicide | Water | | |
| Herbicide Name | (mg) | (ml) | ml/flat ~ | lb/acre* |
| EPTAM® 6E | 53 | 100 | 5 | 0.50 |
| S-ethyl-N,N- | 51 | 50 | 5 | 1.00 |
| dipropylthio | 320 | 100 | 5 | 3.00 |
| carbamate | 1900 | 300 | 4 | 5.00 |
| | 1870 | 300 | 5 | 6.00 |
| SUTAN® 6E | | | | |
| S-ethyl diisobutyl | | | | |
| thiocarbamate | 853 | 100 | 5 | 8.00 |
| VERNAM® 7E | 360 | 400 | 5 | 1.00 |
| S-propyl N,N- | 1798 | 400 | 5 | 5.00 |
| dipropylthio- | 2157 | 400 | 5 | 6.00 |
| carbamate | | | | |

*Rates are calculated on a flat size of 5.75 × 10 × 2.75 inches (14.6 × 25.4 × 7 cm).

Stock solutions of each antidote compound were prepared at the desired concentrations by diluting the requisite amounts of each antidote in acetone. The compositions and rates for each method of application are summarized in Table II.

TABLE II

Antidote Stock Solutions

Phosphonate Antidotes:

| Compositions | | Application | | |
|---|---|---|---|---|
| Antidote (mg) | Acetone (ml) | ml/flat ~ | lb/acre[1] | Method* |
| 10 | 100 | 2 | 0.05 | PPI |
| 30 | 15 | 1 | 0.50 | PPI |
| 40 | 10 | 1 | 1.00 | PPI |
| 40 | 10 | 2 | 2.00 | PPI |
| 320 | 100 | 5 | 4.00 | PPI |
| 40 | 10 | 5 | 5.00 | PPI |
| 95 | 15 | 1.5 | 5.00 | IF |
| 25 | 2.5 | 0.5/10 grams | 0.05 | ST |

TABLE II-continued

Antidote Stock Solutions

Phosphonate Antidotes:

| Compositions | | Application | | |
|---|---|---|---|---|
| Antidote (mg) | Acetone (ml) | ml/flat ~ seed | lb/acre[1] | Method* |

[1]Rates are calculated on a flat size of 5.75 × 10 × 2.75 inches (14.6 × 25.4 × 7 cm).
*PPI = Pre-plant incorporation of herbicide and antidote.
IF = In-furrow surface application.
ST = Seed treatment.

All of the soil used in the tests described herein was loamy sand soil treated with 50 parts per million (ppm) each of cis-N[(trichloromethyl)-thio]-4-cyclohexene-1,2-dicarboximide, a commercially available fungicide, and 18-18-18 fertilizer, which contains 18% by weight equivalent each of nitrogen, phosphorus pentoxide, and potassium oxide.

The thiocarbamate herbicides were applied to the soil by pre-plant incorporation. The antidote compounds were applied by pre-plant incorporation, in-furrow and seed treatment.

For in-furrow (IF) antidote applications, a one pint (473 cubic centimeters) sample of soil from each planting flat was removed and retained. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

For the pre-plant incorporation (PPI) method, the herbicide and the antidote of each test group were each incorporated into the soil prior to planting.

Seed treatment (ST) consists of shaking in a suitable container 10 g. of seed and 0.5 ml. of antidote stock solution.

All flats were placed on greenhouse benches where temperature was maintained between about 70° and about 90° F. (21.1° to 32.2° C.). The flats were watered by sprinkling as needed to assure good plant growth.

Control flats contained crops treated with herbicides only at the various rates and methods of application.

Injury ratings, taken four weeks after application of the antidote, appear in Table III. The effectiveness of the antidote was determined by visual comparison of injuries to crops and weeds in the control and test flats to those in untreated flats.

The treated crops initially screened for diminution of herbicidal injury were milo, wheat, cotton, rice, barley, corn and soybeans. Further testing was conducted on those crops where activity was shown. The weed species tested for control included: foxtail (*Setaria viridis*), Johnsongrass (*Sorghum halepense*), and red oat (Avena sp.).

TABLE III

Antidotal and Herbicidal Effectiveness

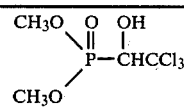

Antidote:
O,O-dimethyl (2,2,2-trichloro-1-hydroxyethyl) phosphonate

| | | | | % Crop and Weed Injury | | | | | | | | | | | | | | | |
|---|---|---|---|---|---|---|---|---|---|---|---|---|---|---|---|---|---|---|---|
| | | Herbicide | | Milo | | Wheat | | Cotton | | Rice | | Barley | | Corn | | Soybean | | Foxtail | | Red Oat | |
| Rate | Method | Name | Rate* | U | T | U | T | U | T | U | T | U | T | U | T | U | T | U | T | U | T |
| 5.00 | PPI | EPTAM | 0.50 | 90 | 98 | 100 | 99 | | | 98 | 99 | 95 | 98 | | | | | 70 | 90 | 100 | 9 |
| 5.00 | PPI | EPTAM | 3.00 | | | | | 80 | 70 | | | | | 80 | 50 | 70 | 30 | | | | |
| 4.00 | PPI | EPTAM | 3.00 | | | | | | | | | 99 | — | 80 | 20 | | | 98 | — | 100 | — |
| 4.00 | PPI | EPTAM | 6.00 | | | | | | | | | 99 | — | 94 | 70 | | | 99 | — | 100 | — |
| 0.50% | ST | EPTAM | 6.00 | | | | | | | | | | | 98 | 90 | | | | | | |
| 1.00 | PPI | EPTAM | 6.00 | | | | | 90 | — | | | 99 | — | 97 | 90 | | | 99 | — | 100 | — |
| 2.00 | PPI | EPTAM | 6.00 | | | | | 90 | — | | | 99 | — | 97 | 70 | | | 99 | — | 100 | — |
| 5.00 | PPI | EPTAM | 6.00 | | | | | 90 | — | | | 99 | — | 97 | 65 | | | 99 | — | 100 | — |
| 1.00 | PPI | SUTAN | 8.00 | | | | | | | | | 99 | — | 75 | 60 | | | 95 | 80 | 100 | — |
| 2.00 | PPI | SUTAN | 8.00 | | | | | | | | | 99 | — | 75 | 35 | | | 95 | 80 | 100 | — |
| 4.00 | PPI | SUTAN | 8.00 | | | | | | | | | 99 | 98 | 75 | 25 | | | 95 | 80 | 100 | — |

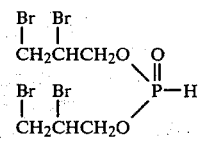

Antidote:
bis-(2,3-dibromopropyl)phosphonate

| | | | | % Crop and Weed Injury | | | | | | | | | | | | | | | |
|---|---|---|---|---|---|---|---|---|---|---|---|---|---|---|---|---|---|---|---|
| | | Herbicide | | Milo | | Wheat | | Cotton | | Rice | | Barley | | Corn | | Soybean | | Foxtail | | Johnsongrass | |
| Rate | Method | Name | Rate* | U | T | U | T | U | T | U | T | U | T | U | T | U | T | U | T | U | T |
| 5.00 | IF | VERNAM | 1.00 | 100 | — | 100 | — | 55 | — | 100 | — | 100 | 85 | | | | | | | | |
| 5.00 | IF | VERNAM | 6.00 | | | | | | | | | | | 90 | 75 | 40 | 100 | | | | |
| 5.00 | IF | VERNAM | 5.00 | | | | | | | | | | | 80 | 5 | | | | | | |
| 0.05 | PPI | EPTAM | 5.00 | | | | | | | | | | | 80 | 60 | | | 100 | — | | |
| 0.05 | PPI | EPTAM | 5.00 | | | | | | | | | | | 60 | 40 | | | | | | |

TABLE III-continued
Antidotal and Herbicidal Effectiveness

Antidote: bis (1,3-dibromoisopropyl)phosphonate

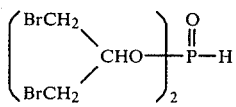

| | | | | % Crop and Weed Injury | | | | | | | | | | | | | | | |
|---|---|---|---|---|---|---|---|---|---|---|---|---|---|---|---|---|---|---|---|
| | | Herbicide | | Milo | | Wheat | | Cotton | | Rice | | Barley | | Corn | | Soybean | | Foxtail | | Johnsongrass |
| Rate | Method | Name | Rate* | U | T | U | T | U | T | U | T | U | T | U | T | U | T | U | T | U | T |
| 5.00 | IF | VERNAM | 1.00 | 100 | — | 100 | — | 55 | — | 100 | — | 100 | — | | | | | | | | |
| 5.00 | IF | VERNAM | 6.00 | | | | | | | | | | | 90 | 75 | 40 | — | | | | |
| 5.00 | IF | VERNAM | 5.00 | | | | | | | | | | | 80 | 0 | | | | | | |
| 0.05 | PPI | EPTAM | 6.00 | | | | | | | | | | | 90 | — | | | 100 | — | 100 | — |
| 0.50 | PPI | EPTAM | 6.00 | | | | | | | | | | | 90 | — | | | 100 | — | 100 | — |
| 5.00 | PPI | EPTAM | 6.00 | | | | | | | | | | | 90 | 15 | | | 100 | — | 100 | — |
| 5.00 | PPI | EPTAM | 1.00 | 100 | — | 100 | — | | | 75 | — | 99 | — | | | | | | | | |
| 5.00 | PPI | EPTAM | 5.00 | | | | | 70 | — | | | | | 90 | 0 | 80 | — | 75 | — | | |

*All rates are shown in pounds per acre. The herbicides were applied by pre-plant incorporation.
Injury Ratings:
U = Antidotally untreated; % injury 4 weeks after herbicide application.
T = Antidotally treated; % injury 4 weeks after treatment with herbicide plus antidote compound.
— = Indicates no change.

Formulations

The object of the formulation is to apply the compounds and compositions to the locus where control is desired by a conventional method. The "locus" may include soil, seeds, seedlings, and vegetation. The compounds and compositions can be formulated in the same manner in which herbicides are generally formulated.

The amount of an antidote compound which comprises part of a herbicidal composition will generally range from approximately 0.001 to 30 parts by weight per weight of the active herbicidal compound.

Formulations will generally contain several additives. Among these are some inert ingredients, diluent carriers, organic solvents, water, oil and water, water in oil emulsions, carriers of dusts and granules, and surface active wetting, dispersing, and emulsifying agents. Fertilizers, e.g., ammonium nitrate, urea and superphosphate, may also be included. Aids to rooting and growth, e.g., compost, manure, humus, sand, etc., may likewise be included. The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters (mm.) in diameter. The granules can be made by spraying a solution of the active ingredient in a volatile solvent onto the granule carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use, the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

We claim:

1. A method of controlling undesirable vegetation while reducing herbicidal injury to crops due to a thiocarbamate herbicide which comprises adding to the soil in which a herbicidally effective amount of said thiocarbamate herbicide is used, (a) a non-phytotoxic antidotally effective amount of a phosphonate of the formula:

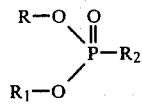

in which
R and $R_1$ are independently selected from the group consisting of alkyl having 1-4 carbon atoms and haloalkyl having 1-4 carbon atoms; and $R_2$ is selected from the group consisting of hydrogen and halohydroxyalkyl having 1-4 carbon atoms; and (b) a herbicidally effective amount of a thiocarbamate of the formula:

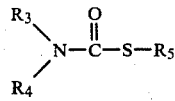

in which
$R_3$ is selected from the group consisting of alkyl having 1-6 carbon atoms and alkenyl having 2-6 carbon atoms;

$R_4$ is selected from the group consisting of alkyl having 1-6 carbon atoms, alkenyl having 2-6 carbon atoms, cyclohexyl and phenyl; or $R_3$ and $R_4$ together form an alkylene group having 5-10 carbon atoms; and $R_5$ is selected from the group consisting of alkyl having 1-6 carbon atoms, haloalkyl having 1-6 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl and substituted benzyl, wherein the substituents are alkyl having 1-4 carbon atoms, haloalkyl having 1-4 carbon atoms and halo.

2. A method according to claim 1 in which R and $R_1$ are each methyl, $R_2$ is 2,2,2-trichloro-1-hydroxyethyl, $R_3$ and $R_4$ are each propyl and $R_5$ is ethyl.

3. A method according to claim 1 in which R and $R_1$ are each 1,3-dibromoisopropyl, $R_2$ is hydrogen, $R_3$ and $R_4$ are each propyl and $R_5$ is ethyl.

4. A method according to claim 1 in which R and $R_1$ are each methyl, $R_2$ is 2,2,2-trichloro-1-hydroxyethyl, $R_3$ and $R_4$ are isobutyl and $R_5$ is ethyl.

5. A method according to claim 1 in which R and $R_1$ are each 2,3-dibromopropyl, $R_2$ is hydrogen, $R_3$ and $R_4$ are each propyl and $R_5$ is ethyl.

6. A method according to claim 1 in which R and $R_1$ are each 1,3-dibromoisopropyl, $R_2$ is hydrogen and $R_3$, $R_4$ and $R_5$ are each propyl.

7. A herbicidal composition comprising (a) a non-phytotoxic antidotally effective amount of a phosphonate of the formula:

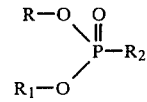

in which
R and $R_1$ are independently selected from the group consisting of alkyl having 1-4 carbon atoms and haloalkyl having 1-4 carbon atoms; and $R_2$ is selected from the group consisting of hydrogen and halohydroxyalkyl having 1-4 carbon atoms; and (b) a herbicidally effective amount of a thiocarbamate herbicide of the formula:

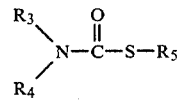

in which
$R_3$ is selected from the group consisting of alkyl having 1-6 carbon atoms and alkenyl having 2-6 carbon atoms;

$R_4$ is selected from the group consisting of alkyl having 1-6 carbon atoms, alkenyl having 2-6 carbon atoms, cyclohexyl and phenyl; or $R_3$ and $R_4$ together form an alkylene group having 5-10 carbon atoms; and $R_5$ is selected from the group consisting of alkyl having 1-6 carbon atoms, haloalkyl having 1-6 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl and substituted benzyl, wherein the substituents are alkyl having 1-4 carbon atoms, haloalkyl having 1-4 carbon atoms, and halo; wherein said antidote compound is present in an amount ranging between about 0.001 to 30 parts by weight for each part by weight of the thiocarbamate herbicidal compound.

8. A composition according to claim 7 in which R and $R_1$ are each methyl, $R_2$ is 2,2,2-trichloro-1-hydroxyethyl, $R_3$ and $R_4$ are each propyl and $R_5$ is ethyl.

9. A composition according to claim 7 in which R and $R_1$ are each 1,3-dibromoisopropyl, $R_2$ is hydrogen, $R_3$ and $R_4$ are each propyl and $R_5$ is ethyl.

10. A composition according to claim 7 in which R and $R_1$ are each methyl, $R_2$ is 2,2,2-trichloro-1-hydroxyethyl, $R_3$ and $R_4$ are isobutyl and $R_5$ is ethyl.

11. A composition according to claim 7 in which R and $R_1$ are each 2,3-dibromopropyl, $R_2$ is hydrogen, $R_3$ and $R_4$ are each propyl and $R_5$ is ethyl.

12. A composition according to claim 7 in which R and $R_1$ are each 1,3-dibromoisopropyl, $R_2$ is hydrogen and $R_3$, $R_4$ and $R_5$ are each propyl.

* * * * *